United States Patent [19]
Nakamura et al.

[11] Patent Number: 5,556,472
[45] Date of Patent: Sep. 17, 1996

[54] FILM DEPOSITION APPARATUS

[75] Inventors: Takao Nakamura; Michitoma Iiyama, both of Osaka, Japan

[73] Assignee: Sumitomo Electric Industries, Ltd, Osaka, Japan

[21] Appl. No.: 454,483

[22] Filed: May 30, 1995

Related U.S. Application Data

[63] Continuation of Ser. No. 987,756, Dec. 9, 1992, abandoned.

[30] Foreign Application Priority Data

| Dec. 9, 1991 | [JP] | Japan | 3-350304 |
|---|---|---|---|
| Dec. 12, 1991 | [JP] | Japan | 3-351671 |
| Dec. 12, 1991 | [JP] | Japan | 3-351672 |
| Dec. 12, 1991 | [JP] | Japan | 3-351673 |
| Apr. 30, 1992 | [JP] | Japan | 4-137789 |
| Dec. 8, 1992 | [JP] | Japan | 4-351724 |

[51] Int. Cl.$^6$ ............................................... C23C 14/00
[52] U.S. Cl. .................... 118/719; 118/725; 118/726; 118/728; 204/298.15; 204/298.25; 204/298.26
[58] Field of Search .................... 118/719, 725, 118/726, 728; 204/298.15, 298.25, 298.26

[56] References Cited

U.S. PATENT DOCUMENTS

| 4,434,189 | 2/1984 | Zapiatynsky | 427/399 |
|---|---|---|---|
| 4,473,455 | 9/1984 | Dean | 118/728 |
| 4,492,852 | 1/1985 | Finegan | 118/725 |
| 4,599,069 | 7/1986 | Murakami | 118/725 |
| 4,693,207 | 9/1987 | Hayakawa et al. | 118/715 |
| 4,950,642 | 8/1990 | Okamoto | 505/730 |
| 5,004,721 | 4/1991 | DeLozanne | 505/730 |
| 5,016,563 | 5/1991 | Murakami | 118/725 |
| 5,033,407 | 7/1991 | Mizuno | 118/725 |

FOREIGN PATENT DOCUMENTS

| 63-179077 | 7/1988 | Japan | 118/725 |
|---|---|---|---|
| 63-295496 | 12/1988 | Japan | 118/715 |
| 1-220875 | 9/1989 | Japan . | |
| 3-60408 | 3/1991 | Japan | 505/732 |
| 3-218906 | 9/1991 | Japan | 118/725 |
| WO89/03125 | 4/1989 | WIPO . | |

OTHER PUBLICATIONS

Zheng, Appl. Phys. Lett. 55 (10), Sep. 4, 1989, pp. 1044–1046.
Dye, Appl. Phys. Lett. 57 (11), Sep. 10, 1990, pp. 1149–1151.
Chan, J. Vac. Sci. Technol. A, vol. 9, No. 5, Sep./Oct. 1991, pp. 2648–2652.
"Low–Temperature Annealing Effect on Bi–Sr–Ca–Cu–O Thin Films Prepared by Layer–by–Layer Deposition", Tsukamoto et al., Japanese Journal of Applied Physics, vol. 30, No. 5A, May 1991, pp. L–830–L–833.
"Superconductivity of $Bi_2Sr_2Ca_{n-1}Cu_nO_y$ (n=2, 3, 4, and 5) Thin Films Prepared In Situ by Molecular–Beam Epitaxy Technique", Nakayama et al., J. Applied Physics, vol. 70, No. 8, Oct. 15, 1991, pp. 4371–4377.

*Primary Examiner*—Richard Bueker
*Attorney, Agent, or Firm*—William L. Feeney; Kerkam, Stowell, Kondracki & Clarke, P.C.

[57] ABSTRACT

A MBE film deposition apparatus comprises a vacuum chamber provided with a partition wall for dividing the vacuum chamber into a first sub-chamber and a second sub-chamber, which are independently provided with a main evacuating apparatus and a auxiliary evacuating apparatus, respectively. The partition wall including an opening for introducing a vacuum impedance for molecular flows between the tint sub-chamber and the second sub-chamber so that a pressure difference can be created between the first sub-chamber and the second sub-chamber when the opening is open. A gate valve is provided on the partition wall for hermetically closing the opening of the partition wall so as to shut off the molecular flows between the first sub-chamber and the second sub-chamber. At least one evaporation source is provided in the first sub-chamber, and a substrate holder is located within the second sub-chamber. A gas supplying apparatus is provided in the second sub-chamber so as to supplying a predetermined gas to the second sub-chamber.

5 Claims, 11 Drawing Sheets

FILM DEPOSITION APPARATUS

This is a continuation of application Ser. No. 07/987,756, filed Dec. 9, 1992, now abandoned.

BACKGROUND OF THE INVENTION

1. Field of the Invention

The present invention relates to a film deposition apparatus, and more specifically to an improved film deposition apparatus suitable in particular for depositing an oxide superconducting thin film or a stacked multi-layer structure including one or more oxide superconducting thin films 2. Description of Related Art Oxide superconductors have been considered to have a critical temperature higher than that of a conventional metal type superconductor, and therefore, to have high possibility of practical use. For example, it has been reported that an Y-Ba-Cu-O compound oxide superconductor material has the critical temperature not less than 80K, and a Bi-Sr-Ca-Cu-O compound oxide superconductor material and a Tl-Ba-Ca-Cu-O compound oxide superconductor material has the critical temperature not less than 100K. The oxide superconductor has a crystalline anisotropy in superconductivity characteristics, and in particular, its critical current density is maximum in a direction perpendicular to a c-axis of crystal lattice. Therefore, when the oxide superconductor is used, attention should be paid to the crystalline orientation.

In the case of applying the oxide superconductor to superconducting electronics including superconducting devices and superconducting integrated circuits, the oxide superconductor has to be used in the form of a thin film. When the oxide superconductor is in the form of a thin film, the above mentioned crystalline anisotropy of superconductivity characteristics becomes more remarkable. In addition, to realize high performance superconducting devices and superconducting integrated circuits, an oxide superconducting thin film having an excellent crystallinity is required.

In order to form the oxide superconducting thin film having an excellent crystallinity, various types of apparatuses such as sputtering, laser ablation and the others have conventionally been used in many cases. However, in the case that a precise film thickness control and a continuous film deposition are required as when an active region of a superconducting field effect transistor type device is formed, it has now been considered that a molecular beam epitaxy (abbreviated "MBE" hereinafter) is optimum. The MBE process enables not only to precisely control a film thickness, by a layer-by-layer deposition, under a ultra-high vacuum, but also to continuously deposit a plurality of oxide superconducting thin films. Therefore, it is possible to form a less disturbed superconducting current path formed of an oxide superconducting thin film, without a large density of unnecessary energy levels, and also to form a sharp junction.

For example, one typical conventional MBE apparatus basically includes a vacuum chamber provided with a main evacuating apparatus, at least one Knudsen's cell (called "K cell" hereinafter) provided at a bottom of the vacuum chamber and for accommodating therein an evaporation source, and a sample holder provided at a top of the vacuum chamber for holding a substrate on which a film is to be deposited. The sample holder is associated with a heater for heating the substrate. In addition, the vacuum chamber is also provided with a port for exchanging a sample, a liquid nitrogen shroud for forming a cold trap around the evaporation source, and a reflecting high energy electron diffraction (called "RHEED" hereinafter) device for observing a thin film roughness during deposition. In front of the substrate held by the sample holder, a shutter is located for controlling the deposition time during the deposition process. In some cases, an electron beam gun (called an "EB gun" sometimes hereinafter) can be provided in place of the K cell. The K cell and the EB gun is provided with an openable shutter.

When an oxide superconducting thin film is deposited in the above mentioned MBE apparatus, a gas supplying apparatus is provided so as to introduce an oxidizing gas such as $O_3$, $NO_2$, $N_2O$, etc. in the proximity of the substrate held by the sample holder. In other words, in order to oxidize metal molecular beams incoming from the evaporation source, it is necessary to supply oxygen in the course of the film deposition so as to maintain an oxygen-enriched atmosphere. Therefore, there is provided the gas supplying device which is not used in conventional MBE apparatuses, so that the oxidizing gas such as $O_3$ is supplied in the proximity of the substrate in the course of the film deposition, whereby a film is deposited while an active oxygen is supplied onto the front surface of the substrate.

However, in the case of manufacturing a superconducting device such as the superconducting field effect transistor type device mentioned hereinbefore and the other type devices, it is required to form a thin film other than the oxide superconducting thin film. The thin film can be exemplified by a thin film of $SrTiO_3$, $Si_3N_4$, etc., used for constituting various insulating films, and by a noble metal film of Au, Pt, etc., used as an electrode. However, it is preferred that these thin films are deposited by a sputtering process, a laser ablation process and a vacuum evaporation process.

On the other hand, if the oxide superconducting thin film is exposed to air, an exposed surface of the oxide superconducting thin film is deteriorated, so that the superconductivity and the crystallinity are destroyed in some cases. In order to avoid this problem, when a different thin film is deposited on the oxide superconducting thin film, a continuous film deposition process has been proposed in which, after the oxide superconducting thin film has been deposited, a different thin film is deposited on the oxide superconducting thin film without being exposed to air.

For example, the continuous film deposition process can be realized by a system in which an MBE apparatus, a sputtering apparatus and a laser ablation apparatus are coupled to one another by a vacuum tunnel, which is in turn connected through an evacuating tube to a vacuum system, so that the MBE apparatus, the sputtering apparatus and the laser ablation apparatus are simultaneously evacuated. The MBE apparatus is additionally provided with another vacuum pump, so that the MBE apparatus can be evacuated to a degree of vacuum higher than that of the sputtering apparatus and the laser ablation apparatus.

With the above mentioned system, a substrate to be deposited can be moved through the vacuum tunnel to any one of the MBE apparatus, the sputtering apparatus and the laser ablation apparatus without being exposed to air.

Furthermore, a load lock type MBE apparatus has been proposed, which mainly includes a vacuum chamber provided with a main evacuating device, a plurality of K cells provided at a bottom of the vacuum chamber and each for accommodating therein an evaporation source, and a sample holder provided at a top of the vacuum chamber for holding a substrate on which a film is to be deposited. In addition, the vacuum chamber is also provided with a liquid nitrogen shroud for forming a cold trap around the evaporation source, and a RHEED device for observing a thin film being deposited. Furthermore, the vacuum chamber is associated with a sample introducing chamber, which is in turn coupled to the vacuum chamber through a gate valve and provided with a sample exchanging port and an auxiliary evacuating device. The gate valve can hermetically shut off communication between the vacuum chamber and the sample introducing chamber.

With this arrangement, when the gate valve is closed so as to maintain a vacuum condition of the vacuum chamber, a substrate is introduced into the sample introducing chamber. After the sample introducing chamber is closed and evacuated by the auxiliary evacuating device until a pressure of the sample introducing chamber is rendered substantially equal to that of the vacuum chamber. Thereafter, the gate valve is opened so that the substrate is moved from the sample introducing chamber to the vacuum chamber. Therefore, the substrate can be introduced into the vacuum chamber and the substrate can be exchanged without breaking the vacuum condition of the vacuum chamber. Accordingly, it is possible to shorten a start-up time of the film deposition processing, and also, contamination of the evaporation source can be effectively prevented.

Here, reviewing the sample holder of the conventional MBE apparatus, the sample holder basically comprises a circular disk member having a front surface integrally provided with a heater and a guide member for guiding and holding a substrate holder. The circular disk member is supported at its rear surface by a tip end of first supporting rods. At the rear surface of the circular disk member, a radiator is supported by second supporting rods. In addition, a pair of power supply wires for supplying an electric power to the heater extend from the rear surface of the circular disk member through the circular disk member to the heater.

Furthermore, the guide member is provided with a plurality of resilient bent members for holding the substrate holder. The substrate holder is in the form of a cap, and a sample or substrate is fixed on an outer surface of a bottom of the cap-shaped substrate holder. An outer surface of an edge portion of a cylindrical section of the cap-shaped substrate holder is provided with a groove. The substrate holder is transported by a magnet coupling transfer rod and is fitted to the tip end of the sample holder by causing the resilient bent members of the guide member to be fitted into the outer groove of the cap-shaped substrate holder. In this condition, the substrate holder is so sized that a predetermined gap is maintained between the heater and an inner surface of the substrate holder when the resilient bent members of the guide member are fitted into the outer groove of the cap-shaped substrate holder. Thus, the gap maintained between the heater and an inner surface of the substrate holder ensures that the fitting and removal of the substrate holder can be smoothly performed.

The film deposition using the above mentioned MBE apparatus is performed in the procedure in which the vacuum chamber is evacuated to a high degree of vacuum (ultra low pressure), and then, the substrate fixed on the substrate holder is heated to a predetermined temperature, and thereafter, the evaporation source is properly heated so that a molecular beam is generated and a thin film is deposited on the substrate.

In the film deposition in accordance with the MBE process, generally, it is necessary to maintain at least the proximity or surrounding of the evaporation sources at a high vacuum of not greater than $10^{-6}$ Torr. On the other hand, if a partial pressure of oxygen on the order of several tens mTorr is not ensured in the neighborhood of the film deposition surface of the substrate, an atmosphere necessary for oxidation cannot be realized. Accordingly, it is necessary to form a sufficient pressure difference between the proximity of the evaporation sources and the neighborhood of the substrate in the single vacuum chamber. However, a satisfactory pressure difference could not be realized.

In addition, the oxide superconducting thin film is transformed from a tetragonal system to an orthorhombic system, and this transformation occurs about 400° C. At this stage, the neighborhood of the deposited film is required to be an oxygen pressure of substantially normal pressures. This can be realized by introducing a large amount of oxygen gas into the vacuum chamber after the film deposition has been completed in the conventional MBE apparatus. However, the evaporation source is oxidized by the introduced oxygen gas and becomes unable to be used again.

Furthermore, if the oxygen gas is introduced in the vacuum chamber to the normal pressures, in order to perform a next film deposition processing, it is necessary to evacuate the vacuum chamber to a ultra-high vacuum, again. Since the evacuation to the vacuum pressure needs a long time, an available time becomes remarkably short.

As mentioned hereinbefore, when a film other than the oxide superconducting thin film is continuously deposited on the oxide superconducting thin film by means of a method other than the MBE process as in the case that the superconducting field effect transistor type device is manufactured, there has been required the system in which the MBE apparatus, the sputtering apparatus and the laser ablation apparatus are coupled to one another. However, this system is realized by coupling the MBE apparatus, the sputtering apparatus and the laser ablation apparatus independently of each other, and therefore, the system is very expensive. In addition, in order to realize a continuous film deposition process, the substrate must be transported from one apparatus to another, and therefore, productivity is low.

In the conventional MBE apparatus, on the other hand, the substrate temperature is limited to about 700° C. at maximum, since the temperature of the deposition surface of the substrate cannot exceed over 700° C. even if the input power to the heater is increased in attempting to deposit the film at a higher substrate temperature. Because of this, it has been difficult to maintain the substrate temperature suitable for deposition of the oxide superconducting thin film.

SUMMARY OF THE INVENTION

Accordingly, it is an object of the present invention to provide a film deposition apparatus which has overcome the above mentioned defects of the conventional ones.

Another object of the present invention is to provide a film deposition apparatus capable of performing the MBE process in which it is necessary to supply an oxidizing gas in the course of a film deposition, as in the case of depositing the oxide superconducting thin film.

Still another object of the present invention is to provide a film deposition apparatus capable of continuously performing not only the MBE process but also a film deposition process other than the MBE process.

A further object of the present invention is to provide a film deposition apparatus capable of setting the substrate temperature at a sufficiently high temperature if desired.

The above and other objects of the present invention are achieved in accordance with the present invention by a film deposition apparatus comprising:

a vacuum chamber provided with a partition means for dividing the vacuum chamber into a first sub-chamber and a second sub-chamber, the partition means including an opening for introducing a vacuum impedance for molecular flows between the first sub-chamber and the second sub-chamber so that a pressure difference can be created between the first sub-chamber and the second sub-chamber when the opening is open;

a gate valve provided on the partition means for hermetically closing the opening of the partition means so as to shut off the molecular flows between the first sub-chamber and the second sub-chamber, at least one evaporation source provided in the first sub-chamber in communication with an internal space of the first sub-chamber;

a main evacuating means coupled to the first sub-chamber for evacuating the first sub-chamber to an ultra-high vacuum;

a substrate holder located within the second sub-chamber for holding a substrate to be deposited;

means for heating the substrate;

a gas supplying means provided in the second sub-chamber so as to supplying a predetermined gas to the front surface of the substrate; and an auxiliary evacuating means coupled to the second sub-chamber for evacuating the second sub-chamber to an ultra-high vacuum when the gate valve is closed.

One preferred embodiment of the film deposition apparatus in accordance with the present invention further includes a sputtering cathode provided in the second sub-chamber of the vacuum chamber and capable of holding a target, and a laser window provided in the second sub-chamber for allowing a laser beam emitted from a laser device located at an outside of the vacuum chamber, to pass through the laser window so as to hit against the target held on the sputtering cathode, whereby a film can be deposited by a selected one of a molecular beam epitaxy, a sputtering and a laser ablation.

In another preferred embodiment of the film deposition apparatus in accordance with the present invention, the substrate heating means includes a heater associated with the substrate holder for heating the substrate held by the substrate holder, and the heater and the substrate holder are so configured that at least one portion of the heater is in direct contact with the substrate. More specifically, at least one of the heater and the substrate holder is resiliently supported to be forcibly contacted with the other of the heater and the substrate.

In still another preferred embodiment of the film deposition apparatus in accordance with the present invention, the substrate heating means includes a heater associated with the substrate holder for heating the substrate held by the substrate holder, and there are further provided an optically transparent window provided in the vacuum chamber, and a beam emitting means located at the outside of the vacuum chamber and for irradiating an infrared or laser beam through the optically transparent window to the substrate held by the substrate holder so as to additionally heat the substrate held by the substrate holder. For example, the optically transparent window is formed in the first sub-chamber at a position opposing to a film deposition surface of the substrate held by the substrate holder, so that the beam emitting means can irradiate the beam through the optically transparent window to the film deposition surface of the substrate held by the substrate holder. Alternatively, the optically transparent window is formed in the second sub-chamber at a position opposing to a rear surface of the substrate held by the substrate holder, so that the beam emitting means can irradiate the beam through the optically transparent window to the rear surface of the substrate held by the substrate holder.

In a further preferred embodiment of the film deposition apparatus in accordance with the present invention, the substrate heating means includes a heater associated with the substrate holder for heating the substrate held by the substrate holder, and there are further provided an electron beam gun or an ion beam gun located within the vacuum chamber and for irradiating an electron beam or an ion ben to the substrate held by the substrate holder so as to additionally heat the substrate held by the substrate holder. For example, the electron beam gun or the ion beam gun is located to oppose to a film deposition surface of the substrate held by the substrate holder, so that the electron beam gun or the ion ben gun can irradiate the ben to the film deposition surface of the substrate held by the substrate holder. Alternatively, the substrate holder is configured to open a rear surface of the substrate held by the substrate holder, and the electron beam gun or the ion beam gun is located to oppose to a rear surface of the substrate held by the substrate holder, so that the electron beam gun or the ion beam gun can irradiate the beam at the rear surface of the substrate held by the substrate holder.

As will be apparent from the above, the film deposition apparatus in accordance with the present invention is characterized in that it comprises the partition means for dividing the vacuum chamber into a first sub-chamber and a second sub-chamber and including an opening for introducing a vacuum impedance for molecular flows between the first sub-chamber and the second sub-chamber so that a pressure difference can be created between the first sub-chamber and the second sub-chamber when the opening is open, the gate valve provided on the partition means for hermetically closing the opening of the partition means so as to completely shut off the molecular flows between the first sub-chamber and the second sub-chamber, and the auxiliary evacuating means coupled to the second sub-chamber for evacuating the second sub-chamber to an ultra-high vacuum when the gate valve is closed.

As mentioned hereinbefore, in the conventional MBE apparatus, since the whole of the vacuum chamber is controlled under a single control system, a sufficient pressure difference could not be created in the vacuum chamber. In addition, if a large amount of oxygen gas were introduced into the vacuum chamber at the time of lowering the substrate temperature, a considerable amount of time is required until the apparatus is brought into a condition capable of starting the film deposition again. Furthermore, if a large amount of oxygen gas were introduced into the single vacuum chamber, the evaporation source is damaged by oxidation and others.

In the film deposition apparatus in accordance with the present invention, however, the molecular flows between the first sub-chamber and the second sub-chamber divided by the partition means within the vacuum chamber is restricted by the partition means having the opening which allows only the restricted molecular flows. Therefore, it i; possible to increase the oxygen partial pressure only in the neighborhood of the substrate. Here, the "restricted molecular flows" can be realized by making the opening to a minimum size which does not prevent passage of a molecular beam.

Incidentally, in view of the object of the RHEED device used in the MBE apparatus, the RHEED device is preferred to be located in the second sub-chamber in which the substrate is located.

Furthermore, the film deposition apparatus in accordance with the present invention includes the gate valve for hermetically closing the opening of the partition means so as to shut off the communication of gas between the first sub-chamber and the second sub-chamber. This gate valve is open in the course of the film deposition, so that the vacuum chamber functions as a single film deposition chamber. However, if the gate valve is closed, the vacuum chamber is completely divided into the first sub-chamber and the second sub-chamber which are hermetically sealed from each other. Therefore, a sufficient amount of oxygen gas can be introduced into the second sub-chamber in which the substrate is located, without introducing the oxygen gas into the first sub-chamber coupled to the evaporation source. Accordingly, the evaporation source is in no way damaged by the oxygen gas.

In addition, since the film deposition apparatus in accordance with the present invention includes the auxiliary evacuating means provided in the second sub-chamber, when the film deposition process is restarted after the processings including the oxygen introduction has been completed, it is possible to evacuate only the second sub-chamber by the auxiliary evacuating means. Accordingly, the film deposition processing can be quickly restarted.

Furthermore, the one embodiment of the film deposition apparatus in accordance with the present invention is constructed so that the MBE apparatus is added with the partition means having the opening for the restricted molecular flows, the gate valve, the auxiliary evacuating means provided for the second sub-chamber, the sputtering cathode and the laser window. In this case, a film can be deposited by any selected one of a molecular beam epitaxy, a sputtering and a laser ablation.

Namely, it is possible to greatly change the pressure in the neighborhood of the substrate since the gate valve is provided in the opening of the partition means. Accordingly, it is possible to perform not only the film deposition by the MBE process requiring a ultra-high vacuum, but also the film deposition by the sputtering and the laser ablation which do not require the vacuum as high as that of the MBE process.

Accordingly, if the film deposition apparatus in accordance with the present invention is used, it is possible to deposit the oxide superconducting thin film having an excellent surface condition by the MBE process, and then, to deposit on the oxide superconducting thin film thus deposited, an insulating film having a high dielectric constant by means of the sputtering process or the laser ablation process by changing the pressure within the same vacuum chamber.

Namely, when different films are continuously performed by different deposition processes in the film deposition apparatus in accordance with the present invention, it is no longer necessary to move the substrate. Therefore, since it is possible to omit the time expensed for the transportation of the substrate and the operation of the system required for the transportation of the substrate, the total deposition time can be improved. In the conventional apparatuses, when the substrate is moved, the substrate temperature is lowered, and when a next film deposition is performed, it is necessary to elevate the substrate temperature from the room temperature to a temperature optimum for the film deposition. On the other hand, in the film deposition apparatus in accordance with the present invention, a next film deposition can be performed by only changing the substrate temperature from a temperature optimum for a preceding film deposition to a temperature optimum for a succeeding film deposition. Therefore, the time required for adjusting the substrate temperature can be shortened. In addition, since the condition of the film deposition can be continuously monitored by the RHEED device, a stacked multi-layer thin film having a high quality can be formed.

In the second embodiment of the film deposition apparatus in accordance with the present invention, since the substrate holder and the heater provided on the bottom of the sample holder are in direct contact with each other, heat can be efficiently transferred or conducted from the heater to the substrate holder. Accordingly, it is possible to perform the film deposition at a high temperature which could not have been realized in the conventional apparatus in which the gap is maintained between the heater and the substrate holder.

In another embodiment of the film deposition apparatus in accordance with the present invention, the heating means includes an ordinary heater associated with the substrate holder and the auxiliary heating means which is located at the outside of the vacuum chamber and configured to heat the substrate by an irradiation heating. With this arrangement, the kind and the specification of the auxiliary heating means can be freely selected if necessary. Accordingly, it is possible to set a substrate temperature which could not have been realized in the conventional apparatus.

The auxiliary heating means can be exemplified by a laser beam or an infrared ray. The irradiation can be realized by irradiating the laser or the infrared light extendedly over a broad area, or by scanning a converged beam so that the whole of the substrate is heated. In addition, if the laser beam or the infrared ray irradiated onto the substrate is optically treated, it is possible to uniformly heat a wider area. In addition, it is also possible to give an arbitrary temperature distribution on the substrate.

In still another embodiment of the film deposition apparatus in accordance with the present invention, the heating means includes an ordinary heater associated with the substrate holder and the auxiliary heating means which is located in the inside of the vacuum chamber and located at a position different from the substrate holding section. Also with this arrangement, the kind and the specification of the auxiliary heating means can be freely selected if necessary. Accordingly, it is possible to set a substrate temperature which could not have been realized in the conventional apparatus.

The auxiliary heating means located in the inside of the vacuum chamber can be constituted of any means which can be used under a ultra-high vacuum as in the vacuum chamber of the MBE apparatus. An electron beam gun and an ion beam gun can be preferably exemplified. These beam guns can be used in a manner of irradiating the beam extendedly over the whole of the substrate, or in another manner of scanning a converged beam so that the whole of the substrate is heated. In addition, if the electron or ion beam irradiated onto the substrate is electromagnetically treated, it is possible to uniformly heat a wider area. In addition, it is also possible to give an arbitrary temperature distribution on the substrate.

The film deposition apparatus in accordance with the present invention having the above mentioned features is very effective in forming a thin film which has to be formed by supplying a reactive gas in the course of the film deposition or just after the deposition of the film has been completed, or which has to be formed with a high substrate temperature. In particular, the film deposition apparatus in accordance with the present invention can be most effectively used for forming an oxide superconducting thin film typified by $Y_1Ba_2Cu_3O_{7-x}$, $Bi_2Sr_2Ca_2Cu_3O_x$ and $Tl_2Ba_2Ca_2Cu_3O_x$. In addition, the film deposition apparatus in accordance with the present invention is also more effective in forming a stacked multi-layer thin film composed of oxide superconducting thin films and another film which is preferred to be formed by a method such as the sputtering and the laser ablation other than the MBE process.

The above and other objects, features and advantages of the present invention will be apparent from she following description of preferred embodiments of the invention with reference to the accompanying drawings;

DESCRIPTION OF THE PREFERRED EMBODIMENTS

Embodiment 1

Figure 1:
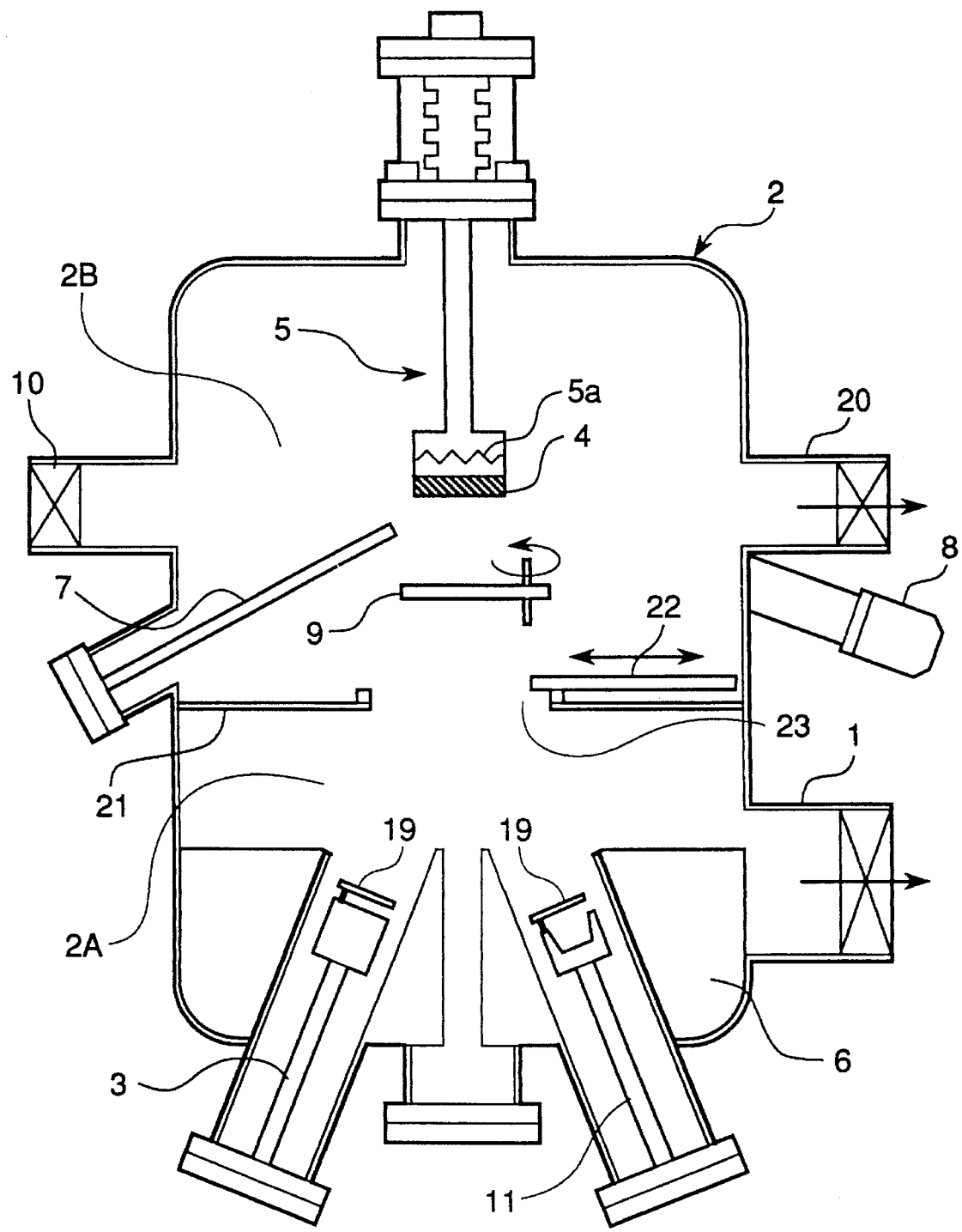
FIG. 1 is a diagrammatic sectional view of a first embodiment of the film deposition apparatus in accordance with the present invention.

Referring to FIG. 1, them is shown a diagrammatic sectional view of a first embodiment of the film deposition apparatus in accordance with the present invention.

The shown film deposition apparatus basically includes a vacuum chamber 2 provided with a main evacuating apparatus 1, at least one K cell 3 and at least one electron beam gun 11 provided at a bottom of the vacuum chamber 2, and a sample holder 5 provided at a top of the vacuum chamber 2 for holding a substrate 4 on which a film is to be deposited. The sample holder 5 is associated with a heater 5a for heating the substrate. In addition, the vacuum chamber 2 is also provided with a port 10 for exchanging a sample, a liquid nitrogen shroud 6 for forming a cold trap around an evaporation source of the K cell, and a RHEED device 8 for observing a thin film roughness during the deposition. In from of the substrate held by the sample holder, a shutter 9 is located for controlling a deposition time during the deposition process. The K cell 3 and the electron beam gun 11 are provided with an openable shutter 19.

In addition, a gas supplying apparatus 7 is provided so as to introduce an oxidizing gas such as $O_3$, $NO_2$, $N_2O$, etc. in the proximity of the substrate 4 held by the sample holder 5, so that the oxidizing gas can be supplied to form an oxygen-enriched atmosphere in the proximity of the substrate 4 in order to oxidize metal molecular beams incoming from the evaporation source in the course of the film deposition.

Furthermore and in accordance with the present invention, the shown film deposition apparatus additionally includes a partition wall 21 for dividing the vacuum chamber 2 into a first sub-chamber 2A which is constituted of a lower portion of the vacuum chamber defined below the partition wall 21 and which is coupled to the K cell 3 and the electron beam gun 11 and the main evacuating apparatus 1, and a second sub-chamber 2B which is constituted of an upper portion of the vacuum chamber defined above the partition wall 21 and in which sample holder 5 is located. The partition wall 21 includes a through opening 23 formed at a center thereof. The position of the opening 23 is determined to ensure that a beam emitted from the K cell 3 and the electron beam gun 11 toward the substrate 4 is not obstructed by the partition wall 21. In addition, the size of the opening 23 is determined to enable restricted molecular flows between the first sub-chamber 2A and the second sub-chamber 2B so that a pressure difference can be created between the tint sub-chamber 2A and the second sub-chamber 2B when the opening 23 is open. Therefore, the partition wall 21 having the through opening 23 constitutes a vacuum impedance. However, the vacuum impedance is in no way limited to the above mentioned partition wall 21 having the through opening 23, and can be constituted by any means which does not obstruct the passage of the beam emitted from the K cell 3 and the electron beam gun 11 toward the substrate 4 and which can realize the restricted molecular flows between the first sub-chamber 2A and the second sub-chamber 2B. In addition, in the shown embodiment, only a single vacuum impedance is provided, but a plurality of vacuum impedances can be succeedingly provided in a cascaded manner.

A gate valve 22 is provided on the partition wall 21 for hermetically closing the opening 23 of the partition wall 21, so as to completely shut off the molecular flows between the first sub-chamber 2A and the second sub-chamber 2B when the gate valve 22 is closed. An opening and closing of this gate valve 22 is controlled from the outside of the film deposition apparatus by a not-shown means.

In addition, an auxiliary evacuating apparatus 20 is coupled to the second sub-chamber 2B for evacuating the second sub-chamber 2B to an ultra-high vacuum when the gate valve 22 is closed. The auxiliary evacuating apparatus 20 can be preferably constituted of a cryopump, since this pump can elevate the degree of vacuum for a short time. In the apparatus actually used by the inventors, with use of a cryopump, the second sub-chamber of the vacuum chamber filled with oxygen to normal pressures could be returned to a pressure on the order of $10^{-6}$ Torr within five minutes.

On the other hand, the main evacuating apparatus 1 can be preferably constituted of a diffusion pump, since capability of the pump is not destroyed even if oxygen is continuously introduced into the chamber for a long time. In the apparatus actually used by the inventors, the vacuum of $10^{-6}$ Torr could be maintained for 10 hours or more by using the diffusion pump having capability of 200 liters per minute.

When an oxide superconducting thin film is deposited by using the above mentioned MBE apparatus, the MBE apparatus can be operated in the following procedures:

First, a substrate 4 is set to the sample holder 5, and an evaporation source is set to the K cell 3. Thereafter, the vacuum chamber 2 is closed, and the gate valve 22 is opened. The vacuum chamber 2 is evacuated by the main evacuating apparatus 1 and the auxiliary evacuating apparatus 20 to an ultra-high vacuum on the order of $10^{-10}$ Torr. In this background pressure, the film deposition by the MBE process becomes possible. Succeedingly, the substrate 4 and the evaporation source are respectively heated by the heater 5a and the K cell 3 to predetermined temperatures. If a molecular beam has become to be stably generated from the evaporation source, the shutter 9 is opened so as to start deposition of a film onto the substrate. At this time, a surface roughness of this deposited film is observed by the RHEED device.

In the course of the film deposition, oxygen is supplied in the form of $O_3$ from the gas supplying device 7.

As mentioned above, the vacuum chamber 2 is provided with vacuum impedance (the partition wall 21 having the through opening 23), a pressure difference of about one digit or more is created between the first sub-chamber 2A and the second sub-chamber 2B. In addition, if it is configured so that the oxygen gas jetted from the gas supplying device 7 is struck onto a deposition surface of the substrate, the oxygen pressure on the deposition surface of the substrate can be further elevated.

If the film deposited on the substrate 4 has reached a predetermined film thickness by the above mentioned processing, the gate valve 22 is first closed, and then, the oxygen gas is introduced into the second sub-chamber 2B until the oxygen pressure in the second sub-chamber 2B elevates to the order of $10^{-1}$ to $10^{-3}$ Torr. In this condition, the substrate 4 is cooled down to at least 400° C., and is maintained in that condition for a while. Thereafter, the substrate 4 is taken out from the second sub-chamber 2B. With this, one film deposition processing is completed.

Thereafter, following the above mentioned film deposition processing, a next new substrate is set to the sample holder, and then, the second sub-chamber 2B is evacuated by the an auxiliary evacuating apparatus 20, so that the next film deposition processing can be quickly started. In addition, in the above mentioned processing, since the first sub-chamber 2A is maintained at the ultra-high vacuum, the evaporation source is in no way damaged.

An $Y_1Ba_2Cu_3O_{7-x}$ thin film was actually deposited by using the above mentioned MBE apparatus, and an excellent thin film having a superconducting critical temperature of 85K or more in an as-grown condition was obtained. The film deposition condition was as follows:

Evaporation sources used: Y, Ba, Cu

Substrate temperature: 700° C.

Gas pressure in the vacuum chamber

First sub-chamber: $1 \times 10^{-5}$ Torr

Second sub-chamber: $5 \times 10^{-6}$ Torr

After the film deposition, the substrate was maintained at the substrate temperature of 400° C. under the oxygen partial pressure of 100 mTorr for 30 minutes.

After the above mentioned film forming process, the time required for reducing the pressure in the vacuum chamber 2 to $10^{-6}$ Torr was five minutes or less. The evacuation was performed by using the cryopump.

Embodiment 2

Figure 2:
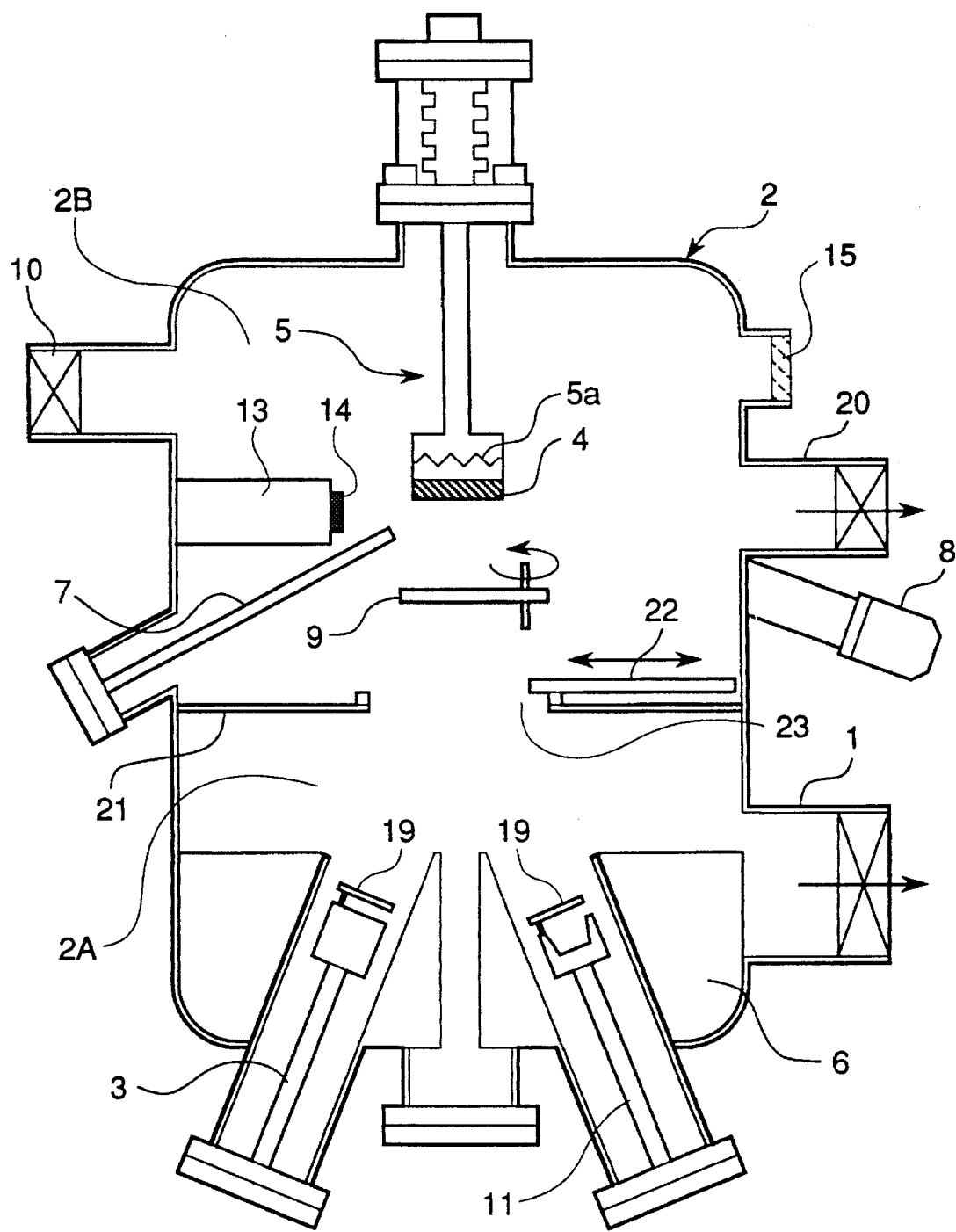
FIG. 2 is a diagrammatic sectional view of a second embodiment of the film deposition apparatus in accordance with the present invention.

Referring to FIG. 2, them is shown a diagrammatic sectional view of a second embodiment of the film deposition apparatus in accordance with the present invention. In FIG. 2, elements similar or corresponding to those shown in FIG. 1 are given the same Reference Numerals, and explanation thereof will be omitted for simplification of description.

As will be apparent from comparison between FIGS. 1 and 2, the second embodiment is characterized in that the vacuum chamber 2 additionally includes a sputtering electrode 13 provided in the second sub-chamber 2B and for holding a target 14, and an incident laser window 15 which is provided in the second sub-chamber 2B and through which a laser beam generated by a laser device (not shown) located at the outside of the vacuum chamber 2 passes so as to irradiate the target 14 held in the sputtering electrode 13. The sputtering electrode 13 is connected to a not-shown radio frequency electric power supply.

When a multi-layer thin film composed of an oxide superconducting thin film and an insulating thin film stacked and deposited on the oxide superconducting thin film is deposited by using the above mentioned MBE apparatus, the apparatus can be operated in the following procedures:

First, a substrate 4 is set to the sample holder 5, an evaporation source is set to the K cell 3, and a target 14 is set to the sputtering electrode 13. Thereafter, the vacuum chamber 2 is closed, and the gate valve 22 is opened. The vacuum chamber 2 is evacuated by the main evacuating apparatus 1 and the auxiliary evacuating apparatus 20 to an ultra-high vacuum on the order of $10^{-10}$ Torr in which background pressure the film deposition by the MBE process is available. Succeedingly, the substrate 4 and the evaporation source are respectively heated by the heater 5a and the K cell 3 to predetermined temperatures. If a molecular beam has become to be stably generated from the evaporation source, the shutter 9 is opened so as to start deposition of a film onto the substrate. At this time, a growing surface roughness of the deposited thin film is observed by the RHEED device.

In the course of the film deposition, oxygen is supplied in the form of $O_3$ from the gas supplying device 7.

As mentioned above, the vacuum chamber 2 is provided with the vacuum impedance (the partition wall 21 having the through opening 23), a pressure difference of about one digit or more is created between the first sub-chamber 2A and the second sub-chamber 2B. In addition, if it is configured so that the oxygen gas jetted from the gas supplying device 7 is struck onto a deposition surface of the substrate, the oxygen pressure on the deposition surface of the substrate can be further elevated.

If the film deposited on the substrate 4 has reached a predetermined film thickness by the above mentioned processing, the gate valve 22 is first closed, and then, the oxygen gas is introduced into the second sub-chamber 2B until the oxygen pressure in the second sub-chamber 2B elevates to the order of $10^{-1}$ to $10^{-3}$ Torr. In this condition, the substrate 4 is cooled down to at least 400° C., and is maintained in that condition for a while.

Thereafter, gas such as argon which can easily generate plasma is introduced into the second sub-chamber 2B, so as to produce the atmosphere having a total pressure of $10^{-1}$ to $10^{-2}$ Torr and a partial pressure ratio of $Ar:O_2=9:1$. In this condition, the substrate temperature is controlled at 600° C. to 650° C., and the electric power is supplied from the radio frequency electric power supply to the sputtering electrode, so that an insulating thin film is deposited on the oxide superconducting thin film formed on the substrate. In the case of depositing the film by the laser ablation process, the atmosphere in the vacuum chamber 2 and the substrate temperature are properly controlled, and thereafter, the laser device (not shown) is operated so as to irradiate the laser beam onto the target 14.

If the insulating film deposited on the oxide superconducting thin film has reached a predetermined film thickness, the radio frequency electric power supply or the laser device is turned off, and also, the heater 5a is turned off. If the substrate 4 is cooled down to room temperature, the substrate 4 is taken out. With this, one film deposition processing is completed. However, in place of terminating the film deposition processing, it is possible to deposit another oxide superconducting .thin film on the insulating thin film by the MBE process, again.

Thereafter, following the above mentioned film deposition processing, a next new substrate is set to the sample holder, and then, the second sub-chamber 2B is evacuated by the an auxiliary evacuating apparatus 20, so that the next film deposition processing can be quickly started. In addition, in the above mentioned processing, since the first sub-chamber is maintained at the ultra-high vacuum, the evaporation source is in no way damaged.

By using the above mentioned second embodiment of the MBE apparatus, an $Y_1Ba_2Cu_3O_{7-x}$ thin film was actually deposited by the MBE process, and a $SrTiO_3$ thin film was also actually deposited on the $Y_1Ba_2Cu_3O_{7-x}$ thin film by the sputtering and/or the laser ablation. In the obtained multilayer thin film, the $Y_1Ba_2Cu_3O_{7-x}$ thin film had a superconducting critical temperature of 85K or more and a boundary between the $Y_1Ba_2Cu_3O_{7-x}$ thin film and the insulating thin film was very excellent. The film deposition condition was as follows:

(1) Deposition condition for $Y_1Ba_2Cu_3O_{7-x}$ thin film
   Evaporation sources used: Y, Ba, Cu
   Substrate temperature: 650° C.
   Gas pressure in the vacuum chamber
   First sub-chamber: $5\times10^{-5}$ Torr
   Second sub-chamber: $5\times10^{-6}$ Torr
(2) Deposition condition for $SrTiO_3$ thin film by the sputtering
   Target: $SrTiO_3$
   Substrate temperature: 600° C.
   Gas pressure in the vacuum chamber: $1\times10^{-2}$ Torr
   Sputtering gas
   Ar: 90%
   $O_2$: 10%
(3) Deposition condition for $SrTiO_3$ thin film by the sputtering
   Target: $SrTiO_3$
   Substrate temperature: 600° C.
   Gas pressure in the vacuum chamber: $1\times10^{-1}$ Torr
   Gas in the vacuum chamber
   Ar: 90%
   $O_2$: 10%

After the above mentioned film forming process, the time requited for reducing the pressure in the vacuum chamber 2 to $10^{-6}$ Torr was two minutes or less. The evacuation was performed by using a sorption pump and the cryopump.

Embodiment 3

Figure 3A:
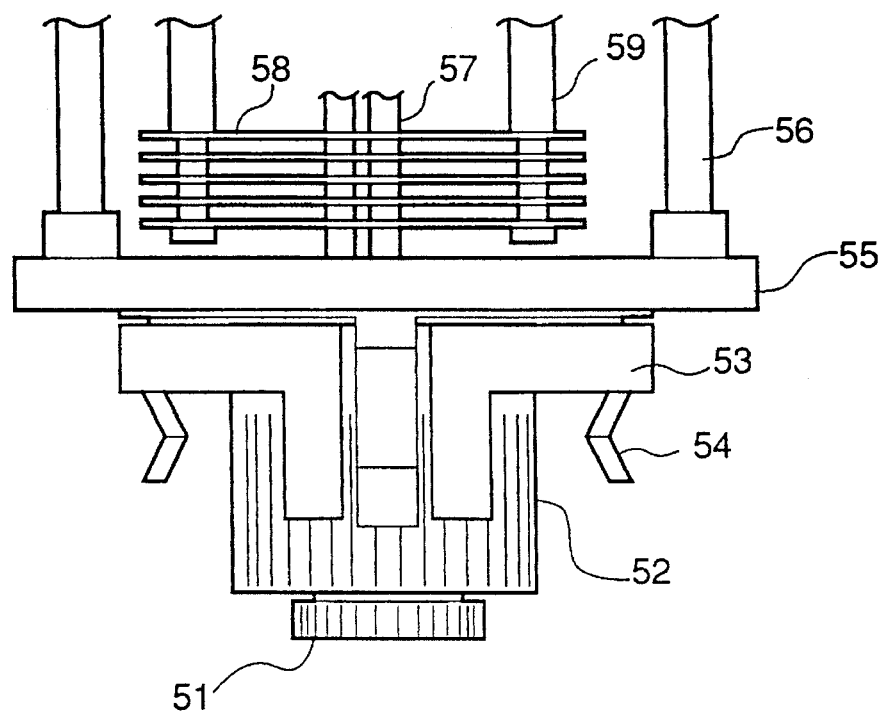
FIG. 3A is a diagrammatic side view of the sample holder incorporated in the film deposition apparatus in accordance with the present invention, in a condition that the substrate holder is removed.
Figure 3B:
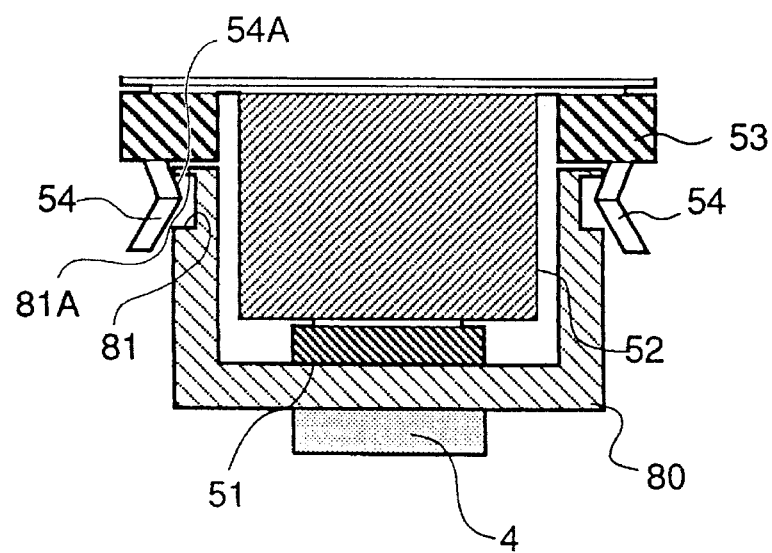
FIG. 3B is a diagrammatic sectional view of a portion of the sample holder shown in FIG. 3A but in a condition that the substrate holder is fined.

Referring to FIG. 3A, there is shown a diagrammatic side view of the sample holder 5 incorporated in the film deposition apparatus in accordance with the present invention, in a condition that the substrate holder is removed, and also referring to FIG. 3B, there is shown a diagrammatic sectional view of a portion of the sample holder shown in FIG. 3A but in a condition that the substrate holder is fitted.

The shown sample holder 5 basically comprises a circular disk member 55 having a front surface integrally provided with an electric heater 52 and a guide member 53 for guiding and holding a substrate holder 80 explained hereinafter and shown in FIG. 3B. The circular disk member 55 is supported at its rear surface by a tip end of first Supporting rods. 56 At the rear surface of the circular disk member 55, radiator 58 is supported by second supporting rods 59. In addition, a pair of power supply wires 57 for supplying an electric power to the heater extend from the rear surface of the circular disk member 55 through the circular disk member 55 to the heater 52.

Furthermore, the guide member 53 is provided with a plurality of resilient bent members 54 for holding the substrate holder 80. As shown in FIGS. 3A and 3B, another heater 51 in the form of a circular disc is mounted on a lower end surface of the heater 52, and the substrate holder 80 is in the form of a cap. A sample or substrate 4 is fixed on an outer surface of a bottom of the cap-shaped substrate holder 80. An outer surface of an edge portion of a cylindrical section of the cap-shaped substrate holder 80 is provided with a groove 81.

The resilient bent members 54 are configured so that when the resilient bent members 54 of the guide member are fitted into the outer groove 81 of the cap-shaped substrate holder 80, the heater 51 is brought into a direct and close contact with an inner surface of the bottom of the cap-shaped substrate holder 80. Namely, the resilient bent members 54 are configured so that an upper surface 54A of a bent portion is in contact with an inner surface 81A of the groove so as to upward bias the substrate holder 80 by a resilient force of the resilient bent members 54.

With the above mentioned arrangement, since the heater 51 and the substrate holder 80 are directly contacted with each other, heat generated by the heater 51 is effectively transferred to the substrate holder 80. In view of this, the bottom of the substrate holder 80 is preferred to be as thin as possible.

A predetermined gap is maintained between the heater 52 and the substrate holder 80, similarly to the conventional apparatus. Accordingly, it never becomes difficult to fit the substrate holder into the sample holder 5 and to remove the substrate holder from the sample holder.

The heater device of the present invention can be realized in other manners. In the above mentioned embodiment, the heater 51 is brought into the substrate holder 80 by contriving the shape of the resilient bent members 54. For example, this arrangement can be modified to the effect that the heater 51 is resiliently supported to be downward biased, so that when the substrate holder 80 is fitted into the sample holder, the heater 51 is resiliently pushed onto the inner surface of the bottom of the substrate holder 80. Alternatively, the substrate holder 80 can be magnetically supported in place of the resilient member 54. Furthermore, the shape of the substrate holder 80 can be modified into a shallow cap, and the position of the groove 81 can be changed. It should be understood that various modifications are included in the scope of the present invention.

With the heating device having the above mentioned structure, it is possible to set the substrate temperature on the order to 900° C.

Embodiment 4

Figure 4:
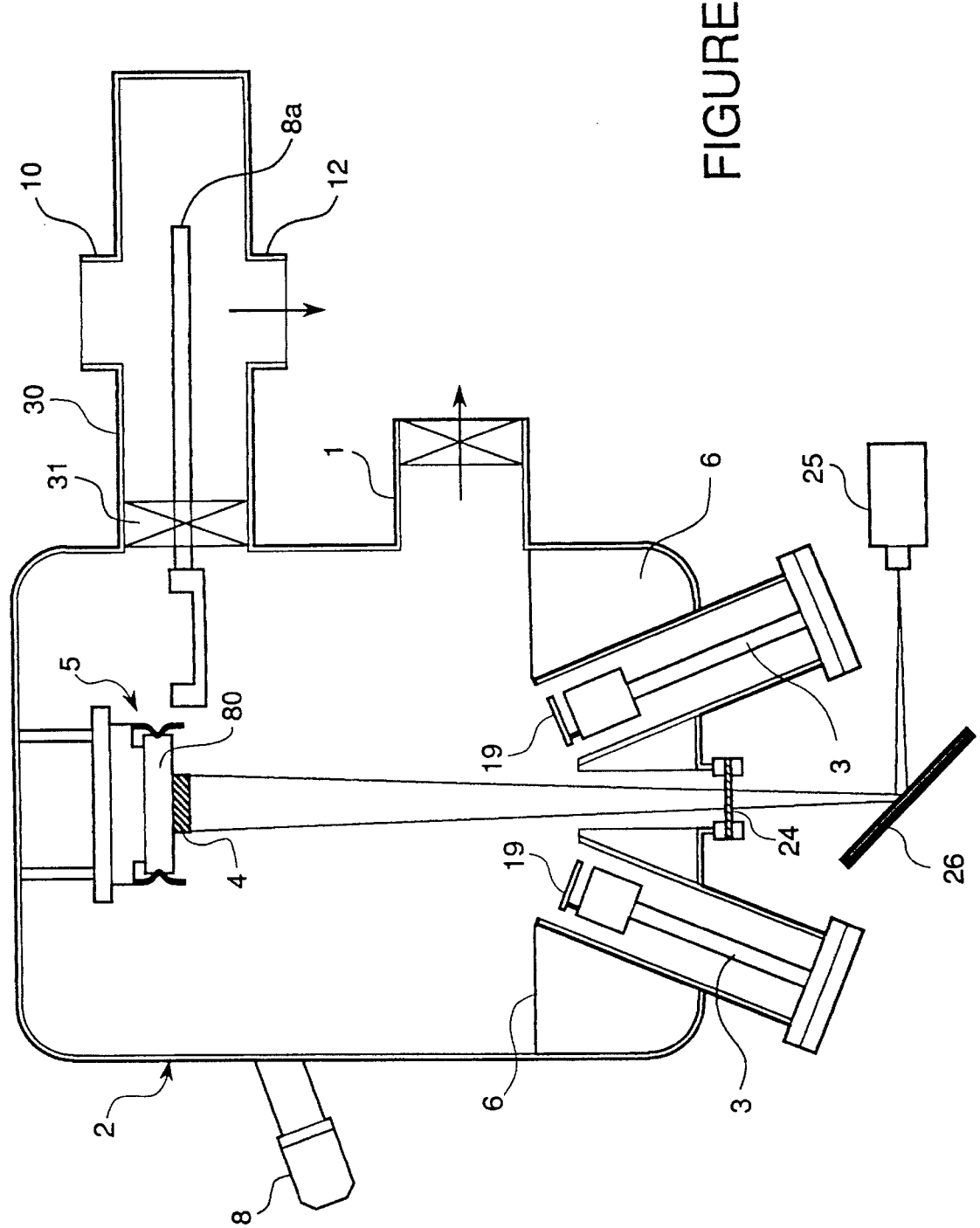
FIG. 4 to 11 are diagrammatic sectional views of other embodiments of the film deposition apparatus in accordance with the present invention.

Referring to FIG. 4, them is shown a diagrammatic sectional view of a fourth embodiment of the film deposition apparatus in accordance with the present invention, which is of the load lock type MBE apparatus. In FIG. 4, elements similar or corresponding to those shown in FIG. 1 are given the same Reference Numerals, and explanation thereof will be omitted for simplification of description.

The shown load lock type MBE apparatus a sample introducing chamber 30, which is in turn coupled to the vacuum chamber 2 through a gate valve 31 and which is provided with a sample exchanging port 10 and an auxiliary evacuating device 12. The gate valve can hermetically shut off the molecular flows between the vacuum chamber 2 and the sample introducing chamber 30.

Furthermore, the substrate heating means provided in the shown load lock type MBE apparatus includes a main electric heater provided in the sample holder similarly to the first and second embodiments, and an auxiliary heating means composed of an optically transparent window 24 hermetically provided in the bottom of the vacuum chamber 2, an optical guide means such as a mirror 26 located below the bottom of the vacuum chamber 2, and a beam emitting device 25 located at the outside of the vacuum chamber 2 and for irradiating an infrared or laser beam through the mirror 26 and the optically transparent window 24 to the substrate 4 held on the substrate holder 80 so as to additionally heat the substrate 4 held on the substrate holder 80.

With this arrangement, when the gate valve 31 is closed so as to maintain a vacuum condition of the vacuum chamber 2, the substrate holder 80 fixed with the substrate 4 is introduced into the sample introducing chamber 30 through the port 10, so that the substrate holder 80 fixed with the substrate 4 is located and held by a tip end of a magnet coupling transporting rod 8a. After the sample introducing chamber 10 is closed and evacuated by the auxiliary evacuating device 12 until a pressure of the sample introducing chamber 30 is rendered substantially equal to that of the vacuum chamber 2. Thereafter, the gate valve is opened so that the substrate holder 80 fixed with the substrate 4 is moved from the sample introducing chamber 30 to the vacuum chamber 2 by moving the transporting rod 8a, and then fitted into the sample holder 5. Furthermore, the transporting rod 8a is drawn back into sample introducing chamber 30, and the gate valve 31 is closed again.

Thereafter, the substrate heating means is energized and the heater in the K cells is also energized so that the MBE process can be performed. In the course of the film deposition, the substrate 4 held on the substrate holder 80 is heated by not only the main electric heater (not shown in FIG. 4) provided in the sample holder 5, but also the beam generated by the beam emitting device 25 and guided by the mirror 26 and the optically transparent window 2a. Since the beam emitting device 25 is located at the outside of the vacuum chamber 2, the beam emitting device 25 can have a sufficiently large output power, a necessary substrate temperature can be easily attained.

When a halogen lamp was used as the ben emitting device 25, the substrate temperature could be elevated up to 800° C.

Embodiment 5

Figure 5:
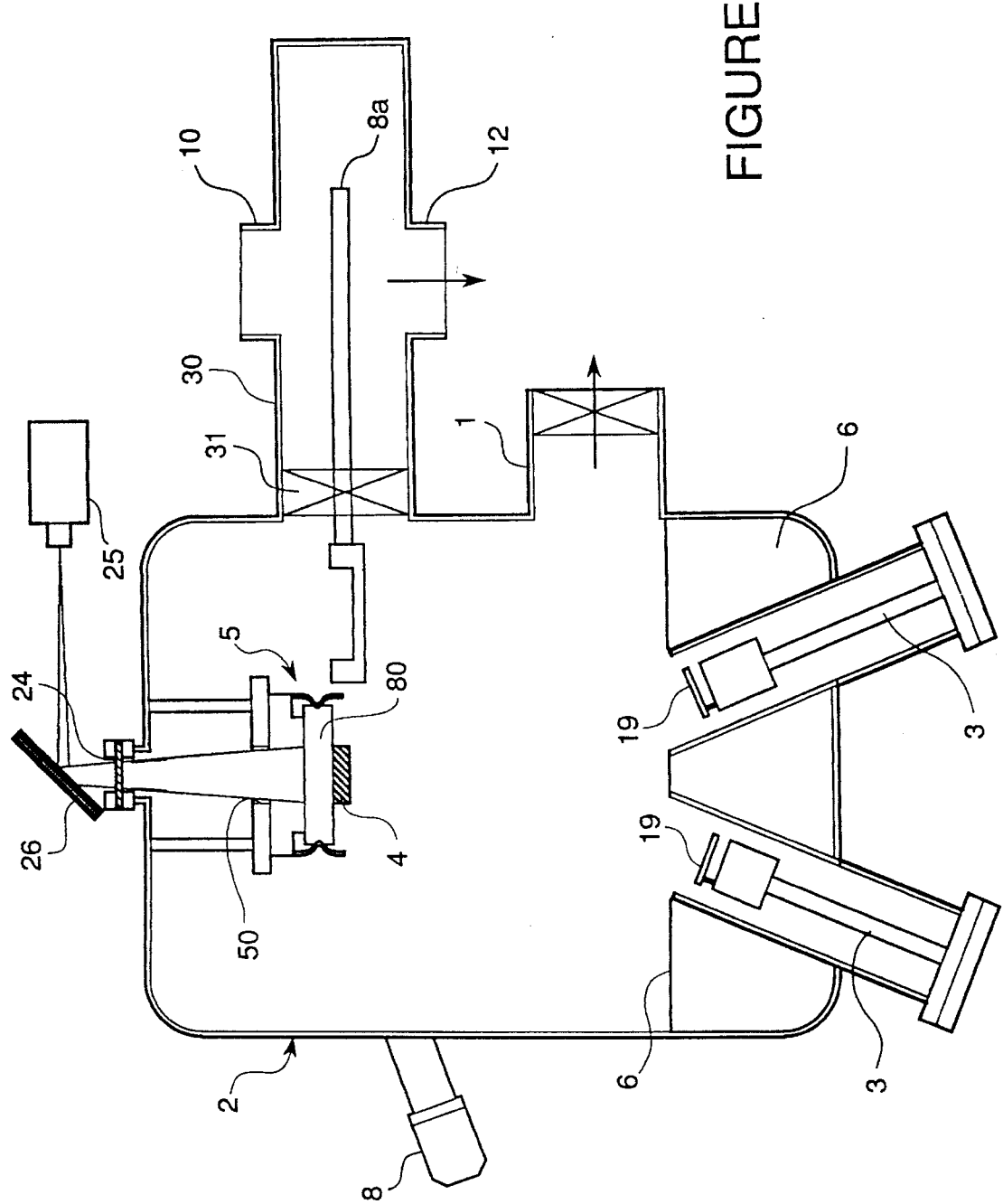

Referring to FIG. 5, there is shown a diagrammatic sectional view of a fifth embodiment of the film deposition apparatus in accordance with the present invention, which is of the lead lock type MBE apparatus. In FIG. 5, elements similar or corresponding to those shown in FIG. 4 are given the same Reference Numerals, and explanation thereof will be omitted for simplification of description.

The fifth embodiment includes the main electric heater (not shown in FIG. 5) provided in the sample holder 5, the optically transparent window 24, the beam emitting device 25 and the mirror 26, similarly to the fourth embodiment. In the fifth embodiment, however, the optically transparent window 24, the beam emitting device 25 and the mirror 26 are located at the same side of the vacuum chamber as the rear surface of the substrate opposing to the film deposition surface, so that the rear surface of the substrate is heated by the beam. Therefore, the sample holder 5 is slightly modified.

For this purpose, the optically transparent window 24 is hermetically provided in the top of the vacuum chamber 2 straightly above the sample holder 5, and the sample holder 5 is so configured that no obstacle exists from the optically transparent window 24 until the rear surface of the substrate holder 80. Therefore, a center through hole 50 is formed in a series of members of the sample holder 5. The center through hole 50 allows energy from beam emitting device 25 to pass from mirror 26 through hole 50 to the rear surface of substrate holder 80. This aids the main electric heater in heating the substrate 4 as apparent from the ray lines of energy striking the rear (upper in FIG.5) of holder 80 such that heat is in turn transferred to substrate 4.

Embodiment 6

Figure 6:
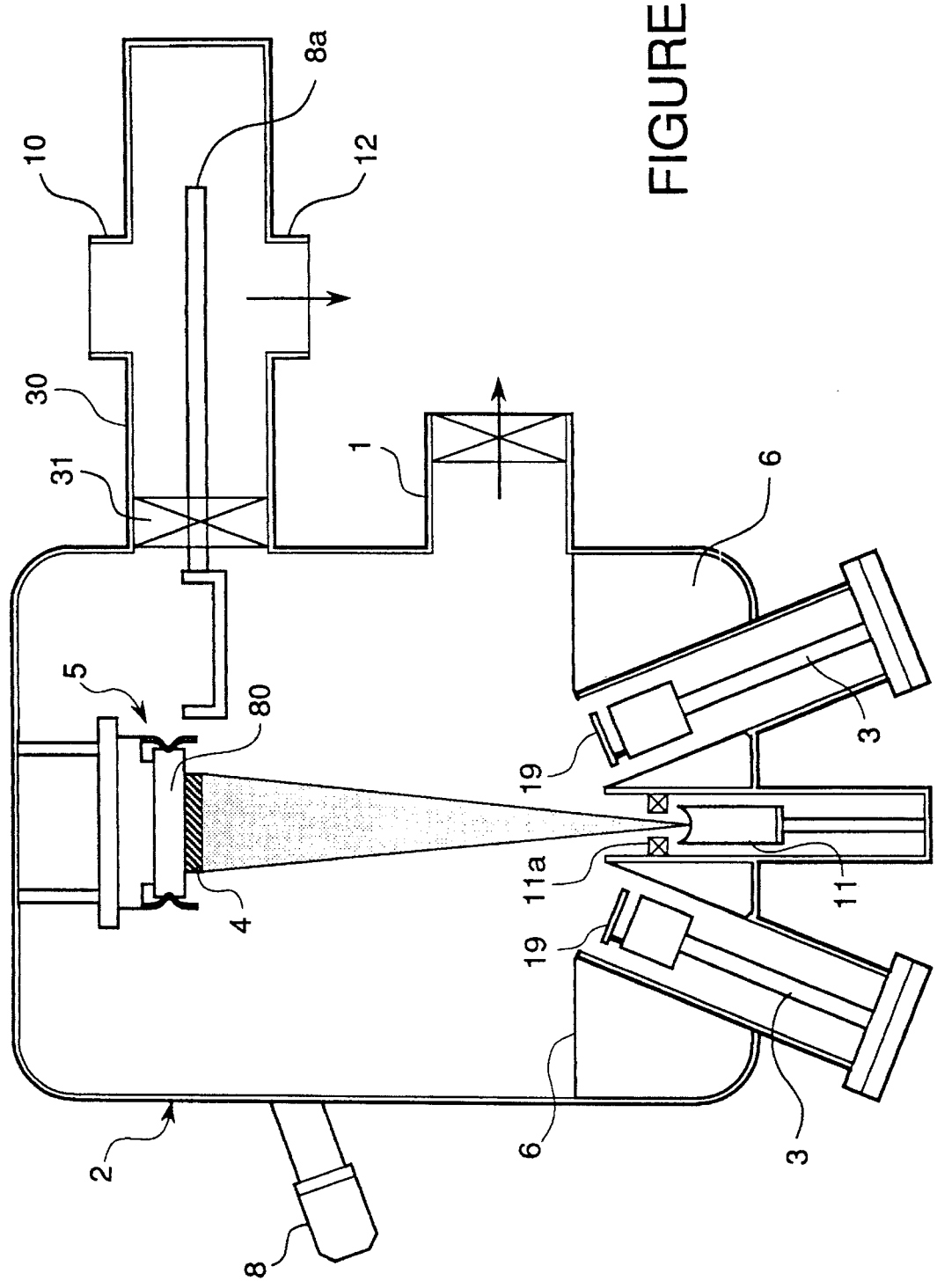

Referring to FIG. 6, there is shown a diagrammatic sectional view of a sixth embodiment of the film deposition apparatus in accordance with the present invention, which is of the load lock type MBE apparatus. In FIG. 6, elements similar or corresponding to those shown in FIG. 4 are given the same Reference Numerals, and explanation thereof will be omitted for simplification of description.

In the sixth embodiment, the auxiliary heating means, which is provided in addition to the main electric heater (not shown in FIG. 5) provided in the sample holder 5, includes an electron beam gun 11 and a coil 11a, which are located within the vacuum chamber 2 and positioned at the bottom of the vacuum chamber 2. For example, the electron beam gun 11 and the coil 11a can be accommodated in a hollow member provided for receiving the K cell.

Thus, electron beam generated by the electron beam gun 11 can be directly irradiated onto the film deposition surface of the substrate 4 held the sample holder S. Here, the electron ben gun 11 used as the auxiliary heating means has any arbitrary size independent of the size of the sample holder 5 and the substrate holder 80, it is possible to easily realize a necessary substrate temperature.

The electron beam can freely focused or scanned by the coil 11a. Therefore, it is also possible to form any desired temperature distribution over the substrate 4, or to uniformly heat the whole of the substrate 4.

In the sixth embodiment, when the electron beam gun having an output of 1.8 KV and 6 A was used, the substrate temperature could be elevated to about 800° C. An ion beam gun can be substituted for the electron beam gun without changing the basic construction of the sixth embodiment.

Embodiment 7

Figure 7:
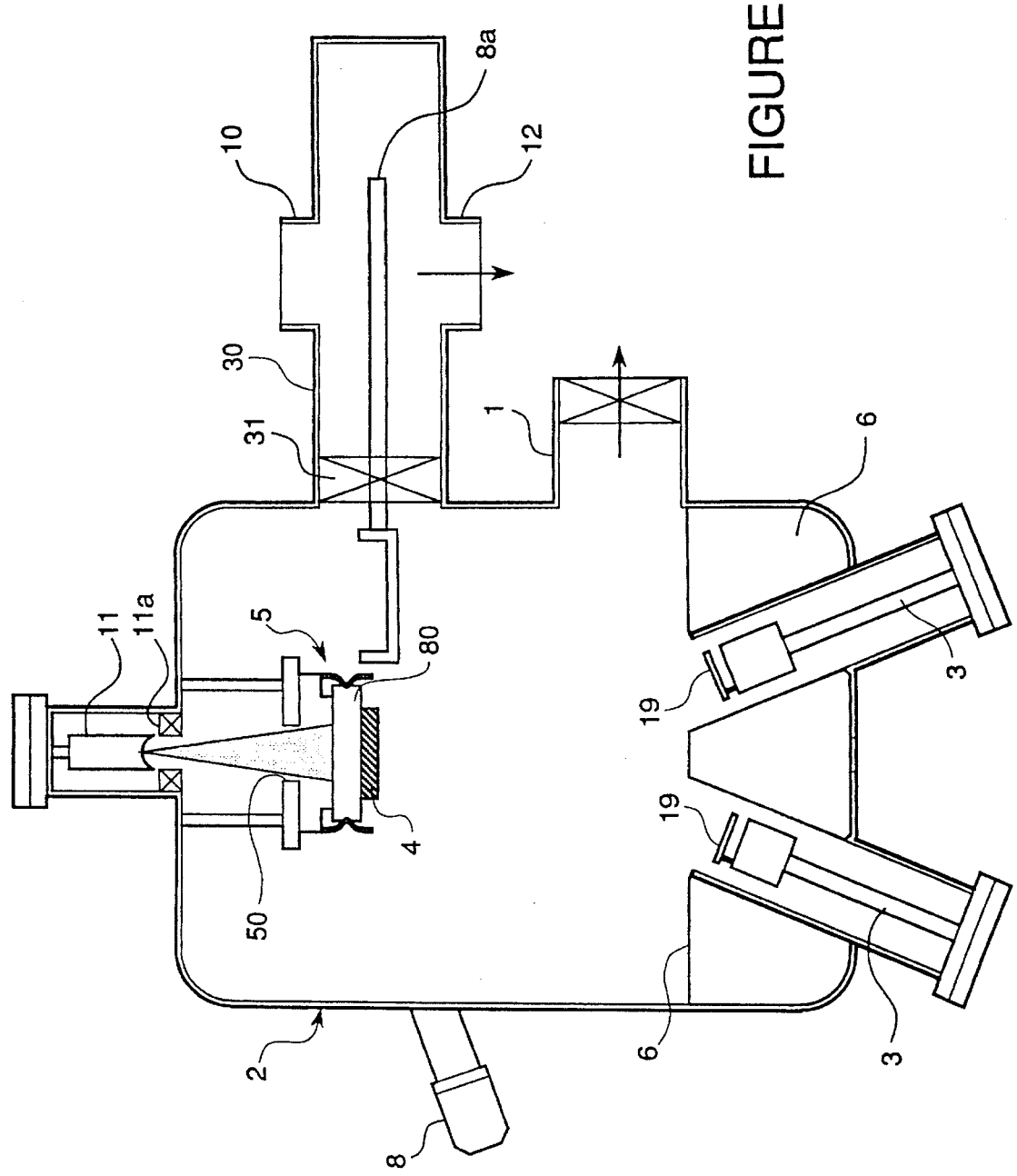
Figure 8:
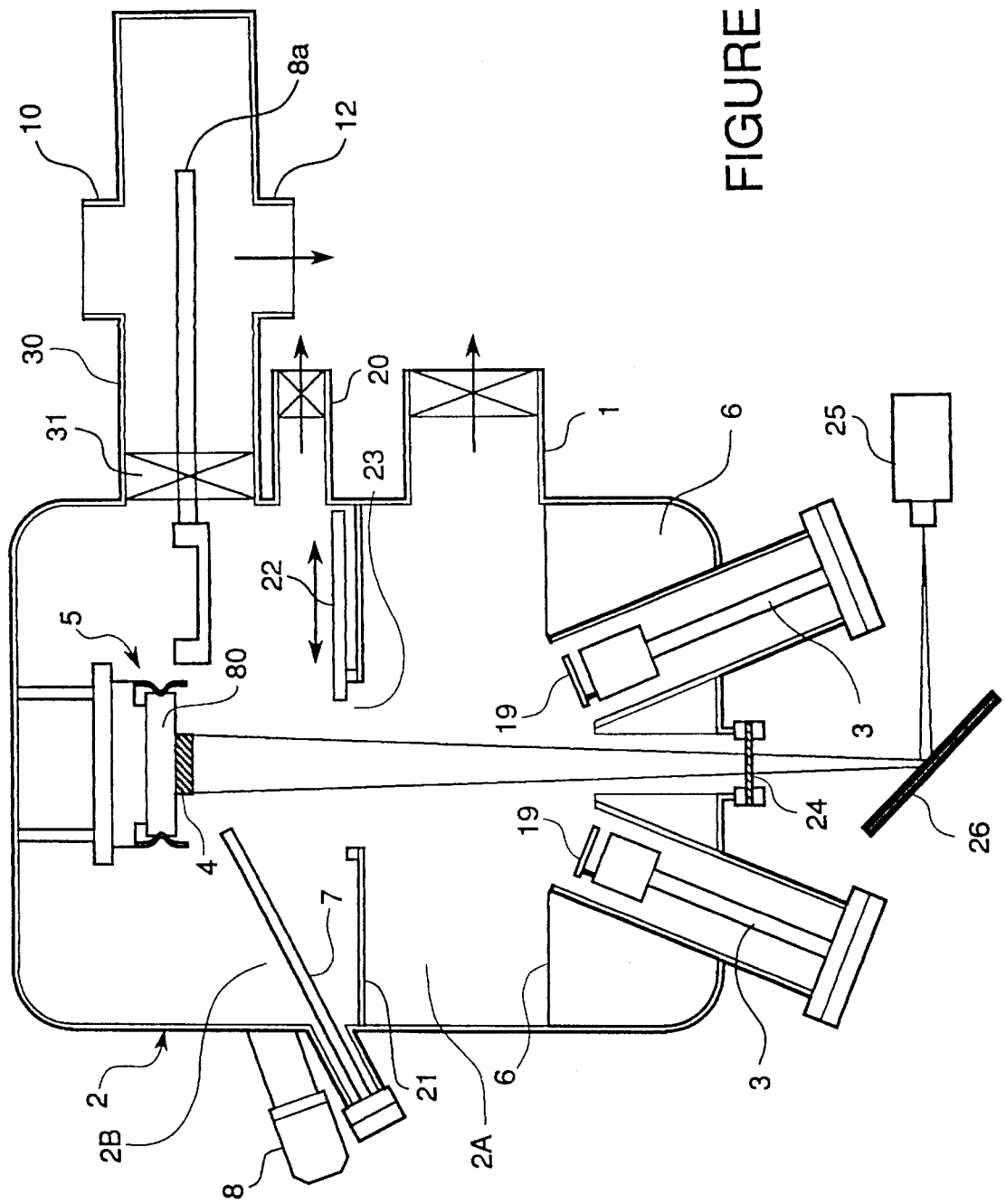
Figure 9:
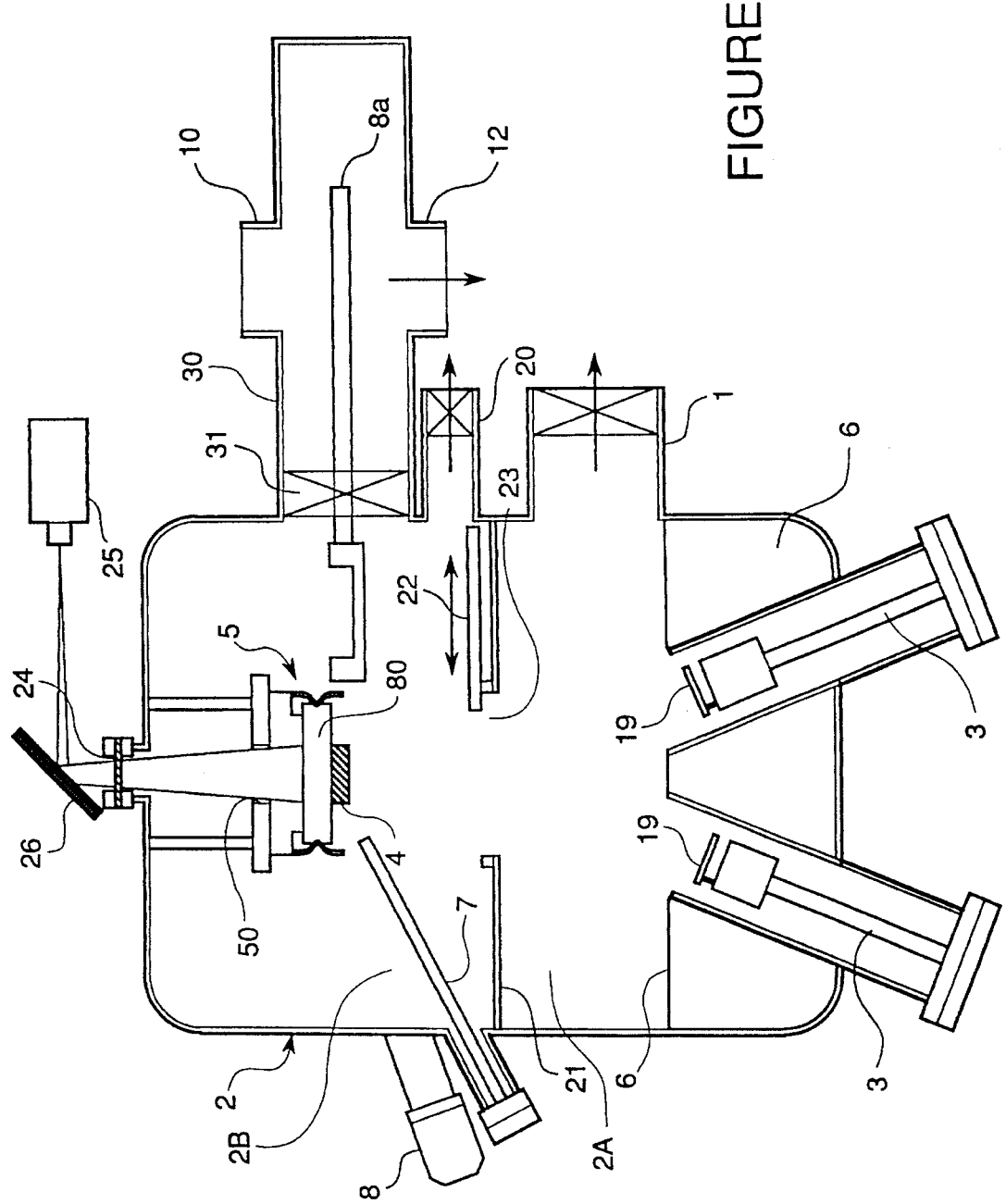
Figure 10:
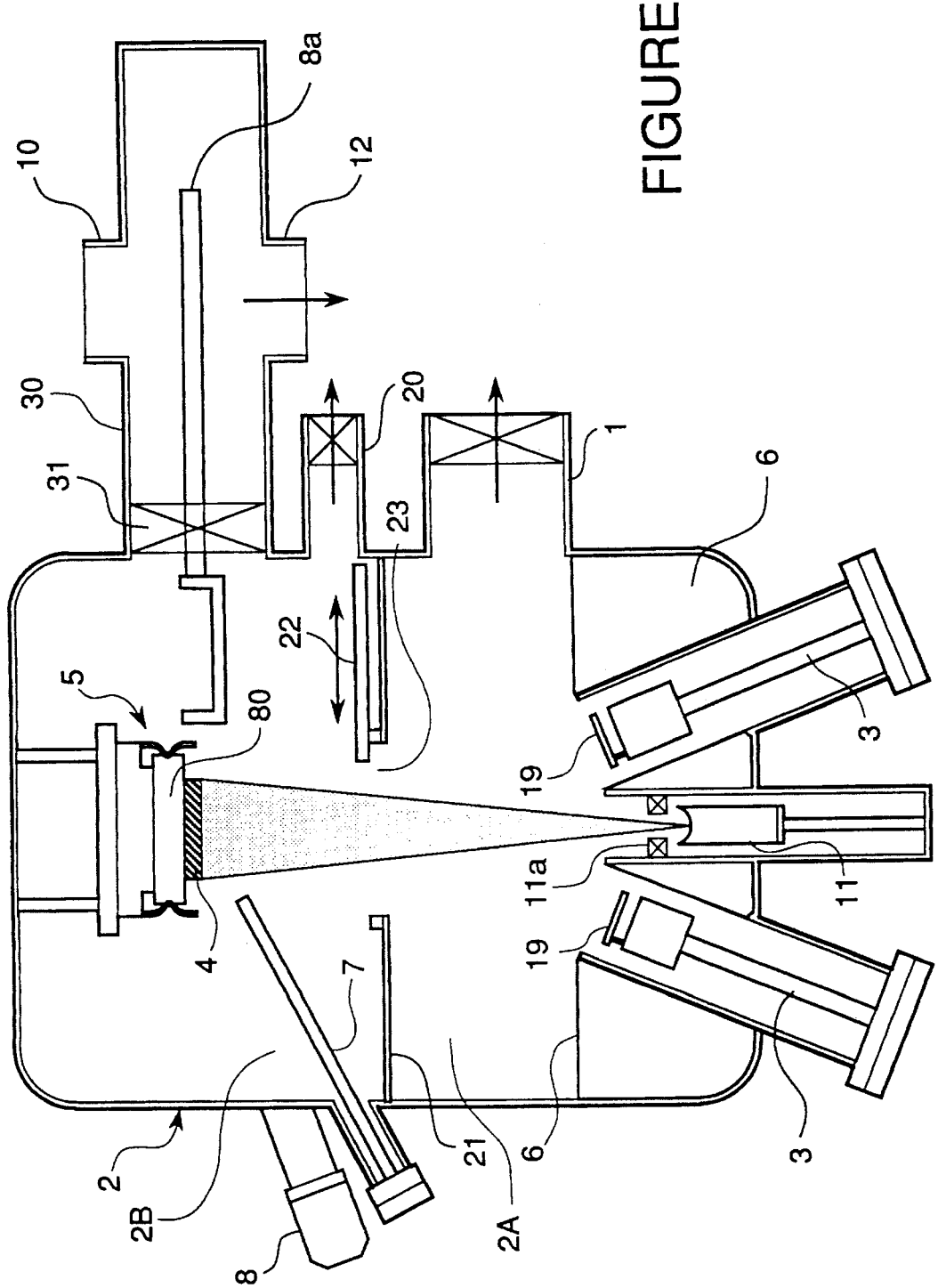
Figure 11:
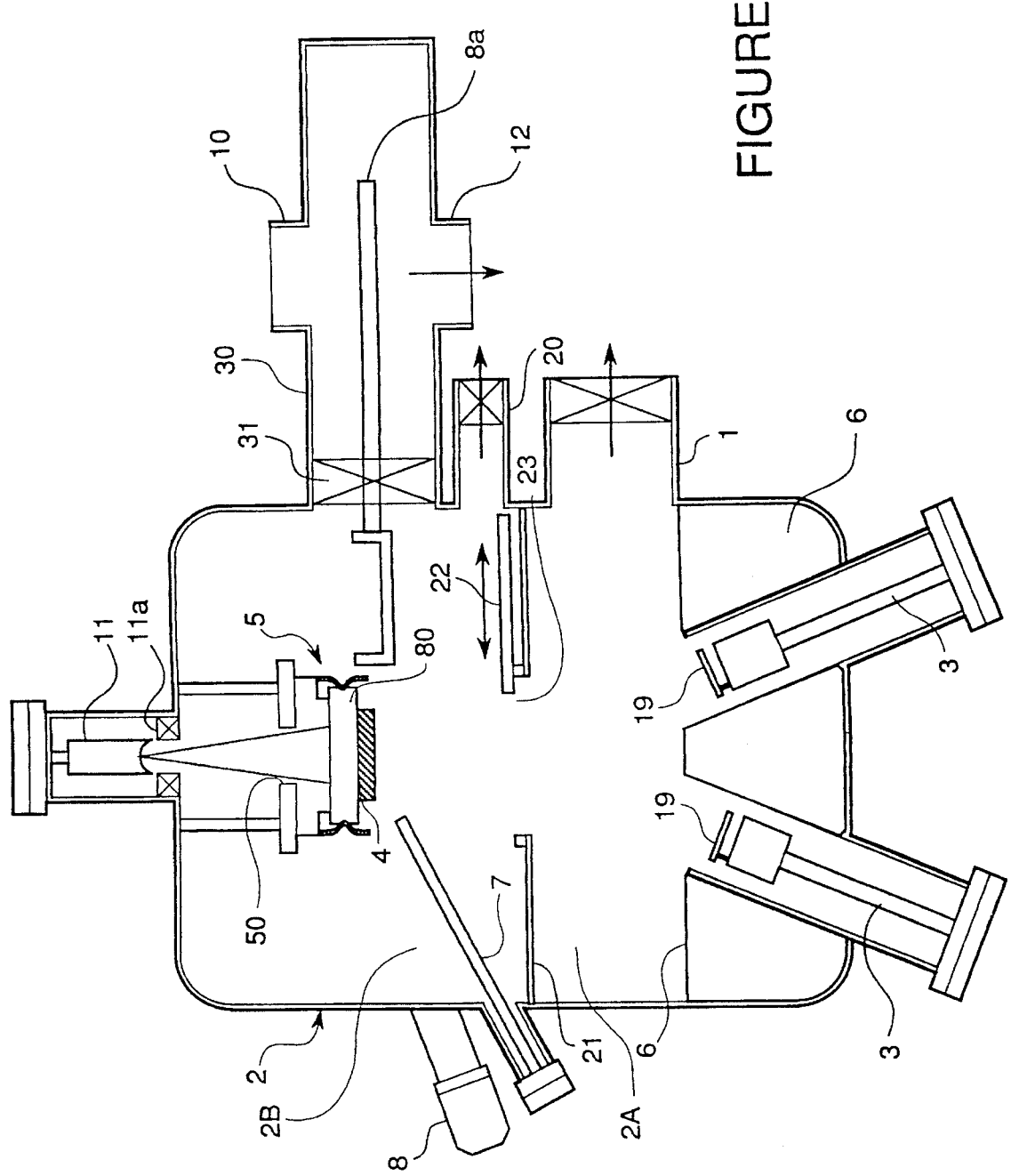

Referring to FIG. 7, there is shown a diagrammatic sectional view of a seventh embodiment of the film deposition apparatus in accordance with the present invention, which is of the load lock type MBE apparatus. In FIG. 7, elements similar or corresponding to those shown in FIG. 6 are given the same Reference Numerals, and explanation thereof will be omitted for simplification of description.

The seventh embodiment includes the main electric heater (not shown in FIG. 5) provided in the sample holder 5, and the electron beam gun 11 internally provided in the vacuum chamber 2, similarly to the sixth embodiment. In the seventh embodiment, however, the electron beam gun 11 is located at the same side of the vacuum chamber as the rear surface of the substrate opposing to the film deposition surface, so that the rear surface of the substrate is heated by the electron beam. Therefore, the sample holder 5 is slightly modified.

For this purpose, the electron beam gun 11 is hermetically provided in the top of the vacuum chamber 2 straightly above the sample holder 5, and the sample holder 5 is so configured that no obstacle exists from the optically transparent window 24 until the rear surface of the substrate holder 80. Therefore, a center through hole 50 is formed in a series of members of the sample holder 5.

Embodiments 8 to 11

Referring to FIGS. 8 to 11, there are shown diagrammatic sectional views of eighth to eleventh embodiments of the film deposition apparatus in accordance with the present invention. In FIGS. 8 to 11, elements similar or corresponding to those shown in FIG. 1 to 7 are given the same Reference Numerals, and explanation thereof will be omitted for simplification of description.

The eighth to eleventh embodiments corresponds the fourth to seventh embodiments combined with the first embodiment shown in FIG. 1. Therefore, since the construction and the operation of the eighth to eleventh embodiments could be easily understood from the explanation of the first and the fourth to seventh embodiments mentioned hereinbefore, explanation of the construction and the operation will be omitted for simplification of description.

In this connection, it could be easily understood that the fourth to seventh embodiments can be combined wish the second embodiment shown in FIG. 2.

As will be apparent from the above, the film deposition apparatus in accordance with the present invention is characterized in that it comprises the partition means for dividing the vacuum chamber into two sub-chambers and having the opening for introducing a vacuum impedance between the two sub-chambers, the gate valve provided on the partition means for hermetically closing the opening of the partition means, and the main and auxiliary evacuating means coupled to the two sub-chambers, respectively. With the partition means having the opening, it is possible to create a sufficient pressure difference between the two sub-chambers. Therefore, the film deposition apparatus in accordance with the present invention can be effectively used for an oxide superconducting thin film deposition which needs to maintain the proximity of an evaporation source at an ultra-high vacuum while supplying an oxygen gas to a front surface on which the oxide superconducting thin film is to be deposited.

If the gate valve is closed, the vacuum chamber is completely divided into the two sub-chambers hermetically sealed from each other. Therefore, a sufficient amount of oxygen gas can be introduced into only the sub-chamber in which the substrate is located, so as to increase the oxygen pressure in the neighborhood of the substrate, while maintaining at an ultra-high vacuum the sub-chamber coupled to the evaporation source. Accordingly, it is possible not only to easily perform the cooling-down treatment of the oxide superconducting thin film, but also to quickly restart the film deposition process.

The above mentioned film deposition apparatus in accordance with the present invention can be very effectively used in forming a thin film deposition which has to supply a reactive gas in the course of the film deposition or just after the deposition of the film has been completed. Therefore, it would be a matter of course that the film deposition apparatus in accordance with the present invention can be utilized for a thin film deposition which needs a treatment using an active gas.

Furthermore, the film deposition apparatus in accordance with the present invention can be configured to additionally include the sputtering electrode and the incident laser window which are provided in the sub-chamber in which the substrate is located. In this case, since the two sub-chambers are completely shut off from each other by closing the gate valve, it is possible to perform the film deposition by the sputtering process and the laser ablation process by supplying a large amount of gas into the sub-chamber in which the substrate is located, so that the pressure in the neighborhood of the substrate is increased. In this time, it is possible to continue to maintain at a ultra-high vacuum the sub-chamber coupled to the evaporation source. Accordingly, it is possible to continuously deposit another film such as an insulating film on the oxide superconducting thin film, and in addition, the film deposition processing can be quickly restarted.

Furthermore, since the film deposition apparatus in accordance with the present invention can set a high substrate temperature, it is possible to deposit various thin films at conditions different from the conventional conditions.

The invention has thus been shown and described with reference to the specific embodiments. However, it should be noted that the present invention is in no way limited to the details of the illustrated structures but changes and modifications may be made within the scope of the appended claims.

We claim:

1. A film deposition apparatus comprising:

a vacuum chamber provided with a partition means for dividing said vacuum chamber into a first sub-chamber and a second sub-chamber, said partition means including an opening for introducing a vacuum impedance for molecular flows between said first sub-chamber and said second sub-chamber so that a pressure difference can be created between said first sub-chamber and said second sub-chamber when said opening is open;

a gate valve provided on said partition means for hermetically closing said opening of said partition means so as to shut of the molecular flows between said first sub-chamber and said second sub-chamber;

at least one evaporation source provided in said first sub-chamber in communication with an internal space of said first sub-chamber;

a main evacuating means coupled to said first sub-chamber for evacuating said first sub-chamber to an ultra-high vacuum;

a substrate holder located within said second sub-chamber for holding a substrate to be deposited;

means for heating said substrate;

a gas supplying means provided in said second sub-chamber so as to supplying a predetermined gas to said second sub-chamber; and an auxiliary evacuating means coupled to said second sub-chamber for evacuating said second sub-chamber to an ultra-high vacuum when said gate valve is closed; and further including a sputtering cathode provided in said second sub-chamber of said vacuum chamber and capable of holding a target, and a laser window provided in said second sub-chamber for allowing a laser beam emitted from a laser device located at an outside of said vacuum chamber, to pass through said laser window so as to hit against said target held by said sputtering cathode, whereby a film can be deposited by a selected one of a molecular beam epitaxy, a sputtering and a laser ablation.

2. A film deposition apparatus claimed in claim 1 wherein said substrate heating means includes a heater associated with said substrate holder for heating said substrate held by said substrate holder, said heater and said substrate holder being so configured that at least one portion of said heater is in direct contact with said substrate.

3. A film deposition apparatus claimed in claim 2 wherein at least one of said heater and said substrate holder is resiliently supported to be forcibly contacted with the other of said heater and said substrate.

4. A film deposition apparatus claimed in claim 1 wherein said substrate heating means includes a heater associated with said substrate holder for heating said substrate held by said substrate holder, and further including an optically transparent window provided in said vacuum chamber, and a beam emitting means located at the outside of said vacuum chamber and for irradiating an infrared or laser beam through said optically transparent window to said substrate held in said substrate holder so as to additionally heat said substrate held in said substrate holder.

5. A film deposition apparatus claimed in claim 4 wherein said optically transparent window is formed in said first sub-chamber at a position opposing to a film deposition surface of said substrate held by said substrate holder, so that said beam emitting means can irradiate said beam through said optically transparent window to said film deposition surface of said substrate held by said substrate holder.

* * * * *

UNITED STATES PATENT AND TRADEMARK OFFICE
CERTIFICATE OF CORRECTION

PATENT NO. : 5,556,472
DATED : September 17, 1996
INVENTOR(S) : Nakamura et al

It is certified that error appears in the above-indentified patent and that said Letters Patent is hereby corrected as shown below:

Title page, [75] Inventors:, change "Michitoma" to -- Michitomo --;

Title page, in the Abstract, line 8 change "tint" to -- first --;

Claim 1, line 12, (column 18, line 43), change "of" to -- off --;

Claim 3, line 4, (column 19, line 14), after "substrate" add -- holder --

Signed and Sealed this

Ninth Day of September, 1997

Attest:

BRUCE LEHMAN

Attesting Officer     Commissioner of Patents and Trademarks